United States Patent
Lowin et al.

(10) Patent No.: US 10,981,016 B2
(45) Date of Patent: Apr. 20, 2021

(54) IDENTIFIABLE MAGNETIC ASSEMBLIES AND COMMUNICATIONS

(71) Applicant: Seraya Medical Systems LLC, Greenwich, CT (US)

(72) Inventors: Leeam Lowin, Greenwich, CT (US); David Leason, Chappaqua, NY (US)

(73) Assignee: SERAYA MEDICAL SYSTEMS LLC, Greenwich, CT (US)

( * ) Notice: Subject to any disclaimer, the term of this patent is extended or adjusted under 35 U.S.C. 154(b) by 30 days.

(21) Appl. No.: 16/351,865

(22) Filed: Mar. 13, 2019

(65) Prior Publication Data

US 2020/0289837 A1    Sep. 17, 2020

(51) Int. Cl.
| | |
|---|---|
| *A61N 2/00* | (2006.01) |
| *A42B 1/04* | (2021.01) |
| *A42B 1/24* | (2021.01) |
| *A61B 5/0476* | (2006.01) |
| *A61B 5/05* | (2021.01) |
| *A61B 5/00* | (2006.01) |
| *A42B 1/242* | (2021.01) |

(52) U.S. Cl.
CPC ............... *A61N 2/006* (2013.01); *A42B 1/04* (2013.01); *A42B 1/242* (2013.01); *A61B 5/0476* (2013.01); *A61B 5/05* (2013.01); *A61B 5/6803* (2013.01)

(58) Field of Classification Search
CPC .......... A61N 2/006; A42B 1/04; A42B 1/242; A61B 5/0476; A61B 5/05; A61B 5/6803
USPC ...................................... 600/9–15
See application file for complete search history.

(56) References Cited

U.S. PATENT DOCUMENTS

| | | | | |
|---|---|---|---|---|
| 6,488,617 B1* | 12/2002 | Katz | ............... | A61B 5/0482 600/26 |
| 8,958,882 B1* | 2/2015 | Hagedorn | .......... | A61N 1/36025 607/45 |
| 2004/0193001 A1* | 9/2004 | Miller | ............... | A61N 2/006 600/9 |
| 2007/0093706 A1* | 4/2007 | Gevins | ............ | A61B 5/6814 600/383 |
| 2010/0113959 A1* | 5/2010 | Pascual-Leone | ...... | A61N 2/008 600/544 |

(Continued)

OTHER PUBLICATIONS

EEG caps Tutorial: Selecting a suitable EEG recording cap, Brain Products GmbH; Version 001, Nov. 10, 2009 (Year: 2009).*

(Continued)

*Primary Examiner* — Navin Natnithithadha
*Assistant Examiner* — Sunita Reddy
(74) *Attorney, Agent, or Firm* — Leason Ellis LLP

(57) ABSTRACT

A method of authorizing performance of transcranial magnetic stimulation on a subject using a head mount adapted to bear one or more magnetic assembly devices having unique identifiers. The method comprises connecting the one or more magnetic assembly devices to a control device, each magnetic assembly device being installed at a location on the head mount, receiving, at the control device, the identifiers of the connected magnetic assembly devices. determining whether the installed magnetic assembly devices are authorized for the treatment based on the received identifiers and treatment configuration information in a database, and energizing the connected magnetic assembly devices based on the determination of authorization.

5 Claims, 8 Drawing Sheets

(56) References Cited

U.S. PATENT DOCUMENTS

| | | | |
|---|---|---|---|
| 2010/0256438 A1* | 10/2010 | Mishelevich | A61N 2/006 600/13 |
| 2012/0157752 A1* | 6/2012 | Nishikawa | A61N 2/006 600/15 |
| 2013/0137918 A1* | 5/2013 | Phillips | A61N 2/02 600/14 |
| 2013/0338424 A1* | 12/2013 | Pascual-Leone | A61N 2/006 600/13 |
| 2014/0276182 A1* | 9/2014 | Helekar | A61B 5/04008 600/544 |
| 2015/0038768 A1* | 2/2015 | Saitoh | A61N 2/006 600/13 |
| 2016/0001096 A1* | 1/2016 | Mishelevich | A61N 7/00 601/2 |
| 2016/0008620 A1 | 1/2016 | Stubbeman | |
| 2016/0015588 A1* | 1/2016 | Tamiya | A61G 15/125 128/845 |
| 2016/0193476 A1* | 7/2016 | Helekar | A61B 5/05 600/544 |
| 2017/0224990 A1 | 8/2017 | Goldwasser et al. | |
| 2018/0071545 A1* | 3/2018 | Saitoh | A61N 1/40 |
| 2018/0350451 A1 | 12/2018 | Leason et al. | |
| 2019/0247662 A1* | 8/2019 | Poltroak | A61B 5/04009 |

OTHER PUBLICATIONS

International Search Report and Written Opinion in corresponding PCT Application No. PCT/US20/22009, dated Jun. 15, 2020.

* cited by examiner

|  | TRANSACTIONS | | DATA BLOCK #1 | | |
|---|---|---|---|---|---|
|  | USED | NEW | | | |
| POSTER END USER A | | 1 | XM3A46F1 (ID 1) | ADD | PARKINSON'S | 25 |
|  | | 2 | AJ287JI02 (ID 2) | ADD | OCD<br>STUTTERING | 15<br>15 |
|  | | 3 | CU192J7G (ID 3) | ADD | PARKINSON'S | 30 |
|  | | 4 | GG98L61B (ID 4) | ADD | MYT DYST | 20 |

FIG. 5A

|  | TRANSACTIONS | | DATA BLOCK #2 | | |
|---|---|---|---|---|---|
|  | USED | NEW | | | |
| POSTER END USER A | 2 | 5 | AJ287JI02 (ID 2) | TREATMENT (OCD) | 2 |
|  | | 6 | AJ287JI02 (ID 2) | ADD | 13 |

FIG. 5B

|  | TRANSACTIONS | | DATA BLOCK #3 | | |
|---|---|---|---|---|---|
|  | USED | NEW | | | |
| POSTER END USER A | 4 | 7 | GG98L61B (ID 4) | TREATMENT (MYT) | 1 |
|  | | 8 | GG98L61B (ID 4) | ADD | 19 |
|  | 1 | 9 | XM3A46F1 (ID 1) | TREATMENT (PARK) | 1 |
|  | | 10 | XM3A46F1 (ID 1) | ADD | 24 |

FIG. 5C

IDENTIFIABLE MAGNETIC ASSEMBLIES AND COMMUNICATIONS

FIELD OF THE INVENTION

The present invention relates to medical devices, and more particularly, relates to a system and method for identifying and controlling use of magnetic assemblies in a Transcranial Magnetic Stimulation (TMS) apparatus.

BACKGROUND OF THE INVENTION

Commonly-owned U.S. patent Ser. No. 10/398,907 B2 entitled "Method and Apparatus for Providing Transcranial Magnetic Simulation (TMS) to a Patient", describes a transcranial magnetic stimulation apparatus ("TMS apparatus") that includes replaceable magnet assemblies that can be used to generate various patterns of transcranial magnetic stimulation. FIG. 1 is a side view of an example TMS apparatus 5. As shown, the TMS apparatus 5 includes a head mount or cap 10 for positioning on a subject's head and a plurality of magnet assemblies 15 that can be attached at specific attachment locations e.g. A, B, C, D, E, F to the surface of the head mount (in FIG. 1, magnetic assemblies are shown attached at locations A, C and E, obscuring the attachment points). The magnet assemblies are connected by leads 25 to a computer device (not shown in FIG. 1). The computer device can be programmed to activate any or all magnet assemblies to generate transcranial magnetic stimulation suited for a specific treatment. For example, the computer device can control magnets at different locations to deliver different magnitudes of stimulation, or to generate particular waveforms of stimulation (e.g., in periodic bursts or oscillatory waves) suited for stimulating activity in specific brain regions.

These waveforms are applied to the magnetic assemblies to set them into motion and to control rotation in order to deliver highly focal stimuli. The various parameters for controlling the magnetic assemblies, which include the waveforms (which can be applied in packet bursts), duty cycles, magnitudes, and rate of rotation, are tailored to the particular treatment or therapy contemplated. As such, the demands on the magnetic assemblies can vary depending on the intended treatment. Commercially available magnetic assemblies preferably are labeled as being approved for particular uses and for a finite number of times before being discarded.

For some medical applications, in order to ensure that a TMS apparatus is used in a medically safe and appropriate manner, it is important that the magnetic assemblies be utilized by licensed medical professionals in an approved way. It is also important that use of the magnetic assemblies operated within their rated number cycles and within the constraints of safe operating parameters since the performance of the assemblies can alter or degrade with repeated use and can degrade in a way that is inappropriate for repair and repackaging as the repaired device may not meet quality control standards.

For other current and envisioned applications of a TMS apparatus, such as home use (unsupervised) for medical purposes, or for non-medical applications such as but not limited to learning and concentration improvement, it is important that the magnetic assemblies be mounted and used properly. Additionally, for such unsupervised uses, the safety concerns outlined above apply with greater urgency.

It would therefore be helpful to provide a way to identify and track the use of particular magnetic assemblies used in a TMS apparatus to ensure that the assemblies are used only for authorized procedures and that the assemblies are not used more than their ratings will permit. The present invention addresses these and other needs.

SUMMARY OF THE INVENTION

Embodiments of the present invention provide a method of authorizing performance of transcranial magnetic simulation on a subject using a head mount adapted to bear one or more magnetic assembly devices having unique identifiers. The method comprises connecting the one or more magnetic assembly devices to a control device, each magnetic assembly device being installed at a location on the head mount, receiving, at the control device, the identifiers of the connected magnetic assembly devices, determining whether the installed magnetic assembly devices are authorized for the treatment based on the received identifiers and treatment configuration information in a database, and energizing the connected one or more magnetic assembly devices based on the determination of authorization.

In certain implementations the database is hosted locally at the control device. In other implementations, the database can be hosted on a cloud platform.

Certain embodiments of the method include verifying the locations of the magnetic devices installed on the head mount. In the determination step, the verified locations can be compared with the treatment configuration data.

Further embodiments comprise receiving, at the control device, for each magnetic assembly device, licensed treatment data. In the determination step the received licensed treatment data is compared with the treatment configuration data.

Additionally, the control device can also receive the number of use limits for authorized uses of each magnetic assembly device. Uses of the one or more magnetic assembly devices can be recorded in a data store, and in a subsequent use of the one or more magnetic assembly devices, it can be determined by interrogating the data store whether a use limit has been reached for any of the one or more magnetic assembly devices.

The transcranial magnetic simulation treatment can be medical or non-medical in nature as described in greater detail below. For example, non-medical stimulation treatments can be designed to improve concentration, memory (short or long term), and learning rate. Medical stimulation treatments can be designed to treat diseases and debilitating conditions such as Parkinson's disease, Myotonic Dystrophy, stuttering, strokes, substance addiction and Obsessive Compulsive Disorder, among other possible conditions amenable to treatment by TMS. Given the portability of the TMS apparatus, the treatments can be performed at facilities or at home.

Embodiments of the present invention also comprise a head mount configured to support a plurality of removably mountable magnetic assembly devices. The head mount comprises an interior sized to be seated on human head, an exterior with a plurality of attachment points, and a circuit component associated with each respective attachment point which provides a unique circuit response, when joined with a magnetic assembly device.

In certain embodiments, the circuit response is dictated solely by the circuit component. In alternative embodiments, the circuit response is a function of both the circuit component and a second circuit component that is affixed to the magnetic assembly device joined to the attachment point.

The circuit response can be one of unique resistance, impedance, capacitance, and inductance. The head mount can further include electrical leads coupled to the attachment points.

Embodiments of the present invention further provide a computer-implemented method for managing a transcranial magnetic stimulation ("TMS") apparatus having a plurality of magnetic assembly devices for providing a treatment, each of the magnetic assembly devices having a unique product ID and being governed for a limited number permitted uses per treatment. The method comprises posting the product ID and the number of permitted uses per treatment to a distributed ledger of a blockchain maintained in a peer-to-peer network for each of the plurality of magnetic assembly devices, receiving a request to use an identified one of the plurality of magnetic assembly devices for a treatment, determining, using a smart contract implemented on a blockchain platform, based on the treatment and the product ID of the magnetic assembly device, whether the device is not licensed for the treatment, or has no further uses left for the treatment, and enforcing the smart contract to prevent additional uses if it is determined that the device is either not licensed for the treatment or has no further uses left for the treatment.

In some implementations, the step of enforcing the smart contract includes sending a notification to at least one of a user and a vendor indicating that only one permitted use of the magnetic assembly device for the requested treatment is left. In other implementations, the step of enforcing the smart contract includes preventing the transcranial magnetic stimulation apparatus from activating the magnetic assembly device.

In certain embodiments, the method further comprises posting a new use transaction on the distributed ledger when it is determined that the device licensed for the treatment and has further uses left for the treatment and updating the distributed ledger to debit the number of uses the device has left after a new use transaction has been posted.

The plurality of magnetic assembly devices can be employed by the transcranial magnetic stimulation apparatus in a manner governed by a protocol that is prescribed for each treatment. The protocol can include a type of stimulation waveform, a magnitude of stimulation, and a duration of stimulation and a prescribed cranial position for specific ones of the plurality of the magnetic assembly devices.

Examples of conditions for which the treatments can be used include the following: Parkinson's disease, stuttering, depression, Myotonic Dystrophy, epilepsy, aphasia, dyslexia, obsessive compulsive disorder and schizophrenia.

To implement the methods disclosed herein, the TMS apparatus is controlled by a control device having a processor operative to execute code for running a blockchain interaction application and a TMS interface. The blockchain interaction application can be operative to generate commands for controlling, directly or indirectly, the operation of the TMS apparatus.

These and other aspects, features, and advantages can be appreciated from the following description of certain embodiments of the invention and the accompanying drawing figures and claims.

BRIEF DESCRIPTION OF THE DRAWINGS

FIG. 5A shows a schematic illustration of an example blockchain transaction data block for posting the magnetic assembly devices listed in Table I herein.

FIG. 5B and FIG. 5C show two examples of subsequent transaction data blocks detailing uses of magnetic assembly devices.

DETAILED DESCRIPTION OF CERTAIN EMBODIMENTS OF THE INVENTION

The following description discloses a method of managing a transcranial magnetic system in which each magnetic assembly device that is used to deliver magnetic stimulation is uniquely identified and licensed restrictions on the use of magnetic assembly devices are enforced. In one implementation, a blockchain methodology is utilized. In another, a ledger is used to track a limit usage. Proper use of licensed treatments is secured by ensuring i) that the configuration of installed magnetic assembly devices correctly matches the prescribed configuration for a treatment to be applied; ii) that each of the magnetic assemblies is authorized for the treatment; iii) that the control device used to drive the magnetic assembly devices is controlled by authorized end user; and that iv) the magnetic assembly devices are not used beyond a prescribed limited number of uses. In another implementation, fewer of these criteria are utilized, such as only i) and iv).

Blockchain provides a non-centralized platform on which transactions can be unalterably recorded in a distributed ledger and validated by participants of the platform. Magnetic assembly devices for use in TMS systems can be provided to end users with unique identification, can be authorized one or more licensed treatment protocols, and for prescribed usage amounts. These device attributes are recorded on the distributed ledger and all following uses of the magnetic assembly devices for treatment are also recorded in the ledger. The blockchain platform is thereby able to monitor and enforce authorized use (e.g. licenses) of the magnetic assembly devices, ensuring that the devices are used in a medically responsible way.

Figure 2:
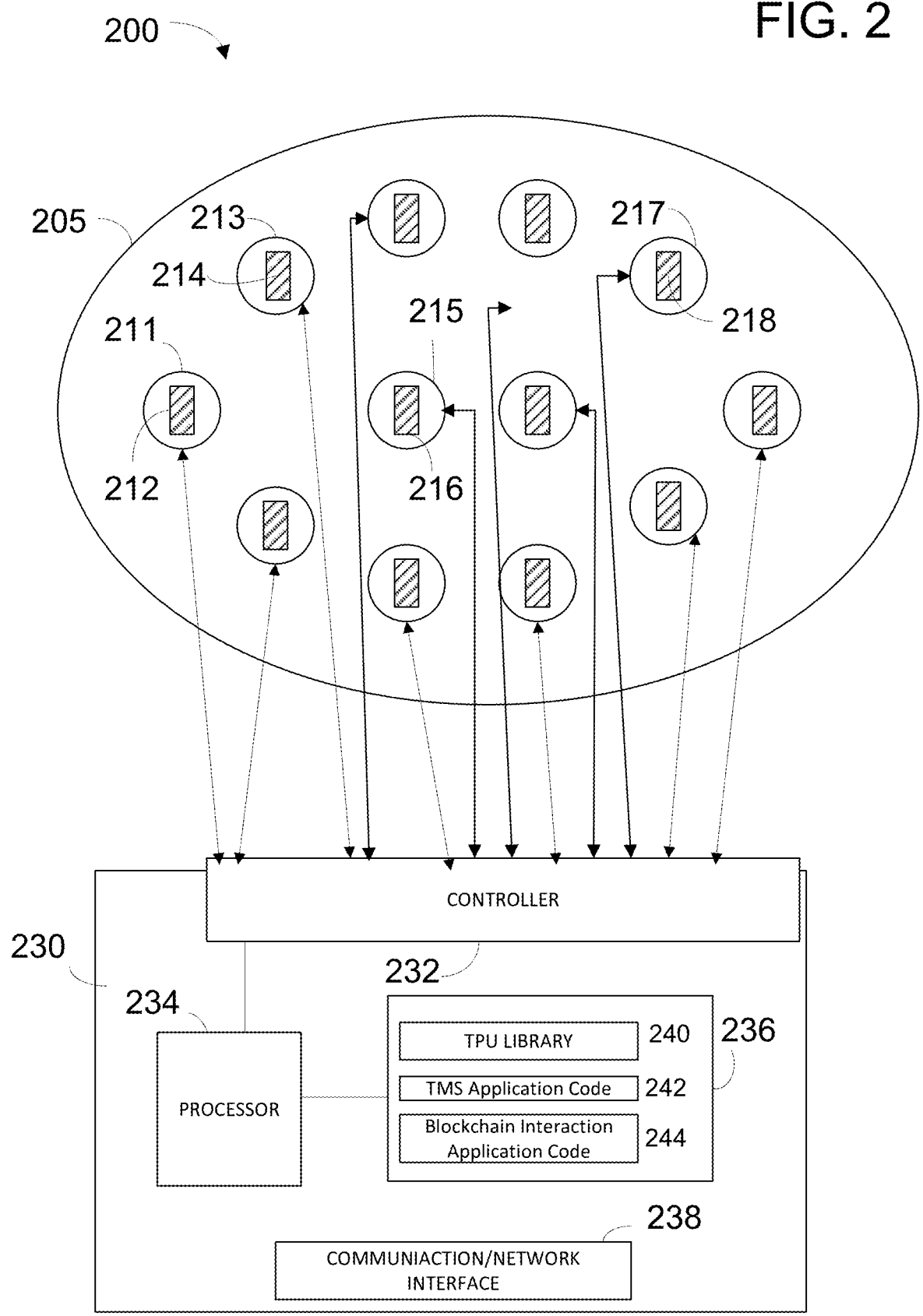
FIG. 2 is a schematic plan view of an example transcranial magnetic system that can be used in the context of the present invention.

FIG. 2 is a schematic plan view of an example transcranial magnetic system 200. A harness, head mount or cap 205 ("head mount") is configured with a plurality of attachment points e.g., 211, 213, 215, 217 where one or more respective magnetic assembly devices 212, 214, 216, 218 can be detachably connected. The attachment points represent specific locations on the head mount and both the number of magnetic assembly devices used, and the positions at which they are deployed at the attachment point on the head mount, depend on the medical conditions (treatment) for which the TMS is applied. In some embodiments, the attachment points can be at predetermined positions on the head mount surface. Alternatively, the head mount can be equipped with rails, channels or similar structures containing conductive elements that enable a given magnetic assembly device to be secured at variable points along the channel or rail, depending on the desired treatment location or the cranial structure of a given subject. In such an embodiment, a rheostat or equivalent circuit can be employed to electronically, identify the variable location of a given magnetic assembly on the head mount 205. The attachment points can all be of like design to permit a standard magnetic assembly device to be attached anywhere along the head mount 205, or the attachment points can provide more than one fitting to only mate with corresponding magnetic assembly devices. The attachment points, 211, 213, 215, 217 which correspond to regions on the cranium where magnetic fields are applied, are optimized for the delivery of magnetic energy for a given diagnosis, therapy, mapping, or other application. The arrangement shown in FIG. 2 is exemplary and it will be appreciated that numerous other configurations can be employed depending on the intended application. The magnetic assembly devices are controlled (i.e., activated, driven and deactivated) by a control device 230 that includes a controller interface 232 ("controller") that is electrically coupled to each of the magnetic assembly devices 212, 214, 216, 218.

Figure 3A:
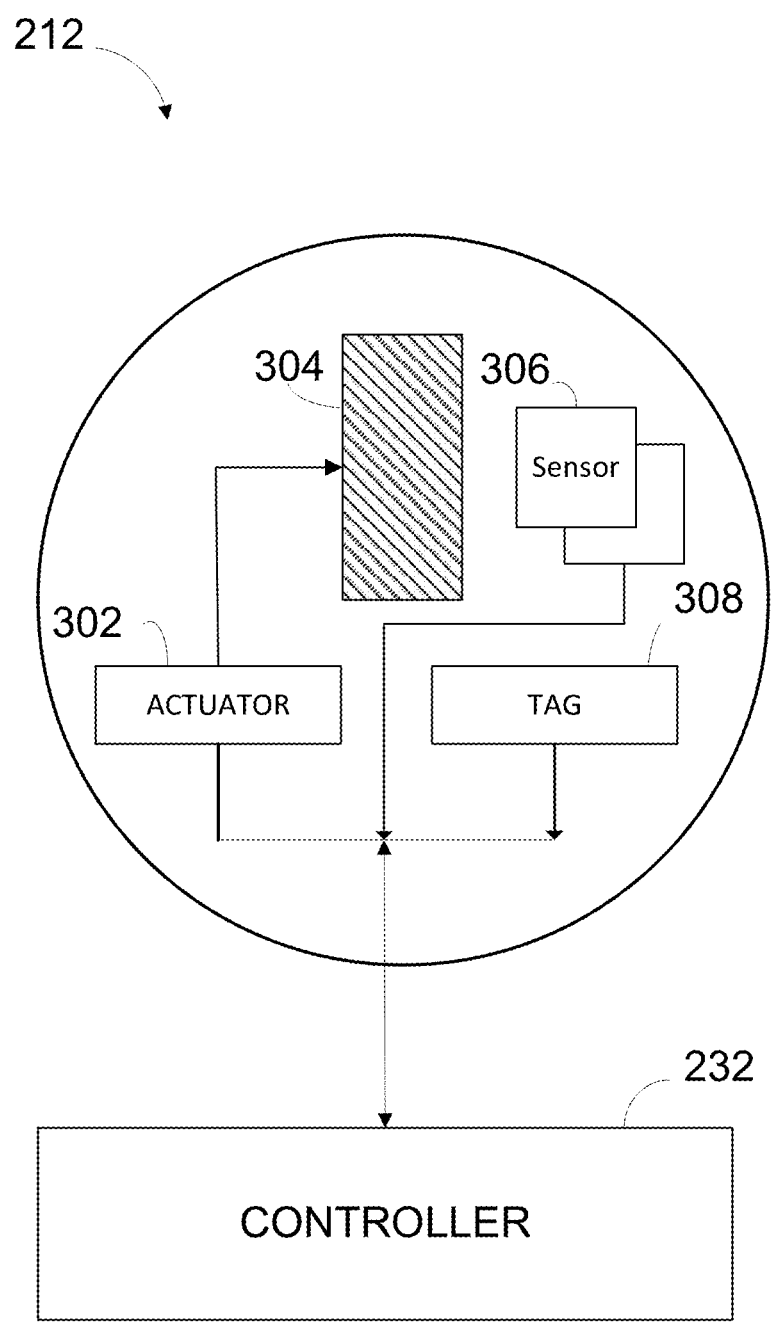
FIG. 3A presents a block diagram illustrating an exemplary magnetic assembly device.

FIG. 3A provides a more detailed illustration of an exemplary magnetic assembly device e.g., 212. The magnetic assembly device includes an actuator device 302 which can be implemented as a motor, such as a stepper or bushed motor that can run at variable speeds. Other actuator device types known to those of skill in the art can be utilized by certain embodiments. The actuator device 302 is electrically coupled to the controller 232 from which it receives electrical signals that drive the actuator device. The actuator device 302 is mechanically and rigidly coupled to a magnet 304, such as via a rotor shaft, and is arranged to cause the magnet 304 to rotate when driven by control signals from the controller 232.

In accordance with various embodiments, the magnet 304 can be of a variety of different types. For example, the magnet 304 can be an electromagnet in which the permeable core is magnetized by electric current, or alternatively, the magnet can be implemented as a permanent magnet. In accordance with a system utilizing one or more permanent magnets, such permanent magnet can be a rare earth, or natural magnet, e.g., a neodymium magnet. In an alternative arrangement, the magnet 304 can be implemented as a soft magnetic composite ("SMC") magnet.

Rotation of the magnet 304 creates a rapidly changing magnetic field about the magnetic assembly device 212. In some embodiments, each of the magnet assembly devices comprises a permanent magnet for selectively providing a rapidly changing magnetic field of at least 500-600 Tesla/second and corresponding to a magnet movement speed of no less than 400 Hertz. As will be appreciated by those knowledgeable in the field of TMS, a weak electric current is induced in neurons within the brain of a subject through the application of a rapidly changing magnetic field of at least 500-600 Tesla/second and corresponding to magnet movement speed of no less than 400 Hertz. These weak electric currents modify the natural electrical activity of the brain, and can be used for a variety of applications. For example, medical applications can include providing a subject with targeted therapies, assisting in diagnosis, mapping out brain function for use in neuroscience research; non-medical applications can include stimulating areas of the brain to improve learning, concentration and education. As defined herein, medical applications can be considered treatments for a subject with a known or possible disease, condition, handicap, or other "sub-normal" attribute, while non-medical application can include those in which the subject may or may not have or be diagnosed of any such conditions or attributes, but wishes to test or improve mental functioning in some manner. It should be understood that for some subjects and in some instances, for example, with respect to subjects having very slight or imagined conditions or handicaps, this distinction can be blurred.

Medical applications include, but are not limited to, Tic Disorders and Tourette Syndrome, Parkinson's disease and other movement disorders such as Dystonia, Tremor and Ataxia, motor neurone diseases such as amyotrophic lateral sclerosis and multiple sclerosis, epilepsy, migraine and other headaches, complex regional pain syndrome (CRPS), neuropathy and fibromyalgia, tinnitus, stroke, psychological disorders including major depressive disorder and treatment resistant depression, anxiety disorders, obsessive compulsive disorder, eating disorders such as anorexia and bulimia, post-traumatic stress disorder (PTSD), psychiatric disorders including schizophrenia and bipolar disorder; visual, auditory and other hallucinations secondary to psychiatric disorders, attention disorders such as ADHD, substance abuse and addictions, learning disorders such as dyslexia and dysgraphia; speech disorders such as stuttering, memory disorders, dementia including Alzheimer's disease, traumatic brain injury, autism spectrum disorder, disorders of consciousness, and urinary incontinence.

Non-medical applications include, but are not limited to improvement or other modulation of: mood; attention and focus; motor and cognitive functions; anxiety such as social shyness; depression; memory and learning; smoking cessation, alcoholism and other addiction; and PTSD.

In one exemplary configuration of the magnetic assembly device, the actuator device 302 may comprise both a motor for rotating the magnet and a lateral movement device (not shown) for changing the position of the magnet relative to the subject, such as solenoid. In this exemplary configuration, the lateral movement device in the magnetic assembly device can position the magnet closer or further away from brain of the subject. Whether and when there is lateral movement can be dependent upon particular treatment parameters that a user is applying to the subject. The lateral movement device optionally enables azimuth adjustment in addition to or as the lateral movement itself.

The magnetic assembly device 212 also includes one or more sensors 306 that can be used to monitor the magnetic field or the temperature of the assembly device, the current induced in the brain, or other data points regarding the assembly or the subject. Such data can comprise biophysical data as is known to those of skill in the art. In one arrangement, the sensors 306 comprise an array of one or more electrodes that are configured to measure electrical activity of the brain and to send the measured data as electrical signals back to the controller 232. The data gathered can be packaged, if desired, and uploaded to a persistent data store, which may be local or remote to the control device, e.g., to serve as supporting data with regard to the safety or efficacy of a particular treatment protocol unit or treatment protocol. Additionally, magnetic assembly device 212 includes an identification element, such as an RFID or QR tag and/or a memory unit (chip or card) that uniquely identifies each device. The memory unit is coupled to a standard port to allow the memory unit to be read externally. In some embodiments, the tag can be placed on the outer housing of the device or other accessible location. In other embodiments, the memory unit can be read by the controller 232 in order to determine the identifier of the magnetic assembly device.

Returning to FIG. 2, the controller 232 communicates with one or more of the magnetic assembly devices 212, 214, 216, 218 through a wired or wireless link or combinations thereof. The controller 232 communicates with the magnetic assembly devices using separately controllable communication links, one for each magnetic assembly device e.g., 212, 214. In addition, in some embodiments, the controller 232 can receive electrical signals from the attachment points e.g., 211, 213, 215, 217 whenever the magnetic assembly devices are being deployed. In certain configurations, however, the controller 232 can communicate with the magnetic assembly devices through the use of various combinations of one or more conduits, USB, serial, or wired or wireless communication links that are known to those of ordinary skill in the art.

Figure 3B:
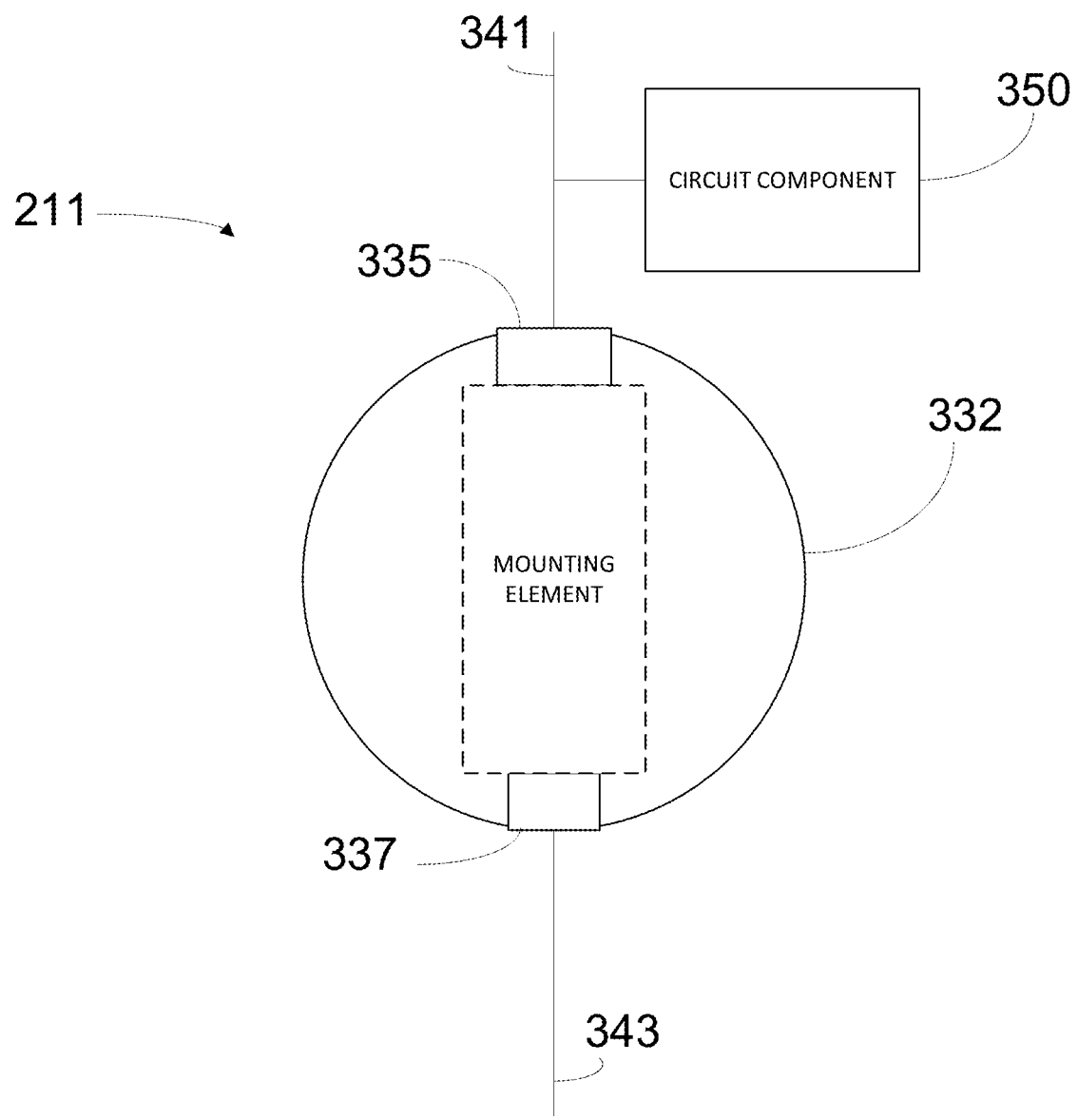
FIG. 3B is a schematic block diagram of an attachment point of a head mount according to an embodiment of the present invention.

FIG. 3B illustrates an exemplary embodiment of an attachment point 211 that can be used in the context of the present invention. Attachment point 211 includes an opening 332 in which a mounting element of a magnetic assembly device can be received (an example mounting element is shown in outline). Electrical contacts 335, 337 can be disposed at opposite edges of opening 332, as shown. A first electrical lead 341 is coupled to electrical contact 335, and a second electrical lead 343 is coupled to electrical contact 337. The controller 232 is coupled to the electrical leads 341, 343. A circuit component 350, which can be a resistor, capacitor, or inductive element, is coupled to electrical lead 341 and has a second coupling to cause the component to either be in parallel or in series with any particular mounted magnitude assembly device. When the mounting element of a magnetic assembly device is mounted into the opening, the mounting element, which is conductive, effectively closes the circuit by allowing current to flow in the channel between the contacts 335, 337 and the electrical leads 341, 343. In addition, when the magnetic assembly device is mounted, and the circuit is closed, a current or voltage signal flowing is modified by the circuit component 350 which is arranged either in parallel with the channel through the attachment point or in series, depending on the particular implementation. The properties of the circuit component 350 are chosen to be (e.g., resistance, impedance, capacitance, reactance) unique to the attachment point. Accordingly, the magnitude, phase, or both magnitude and phase of the modification of the current/voltage signal by the component of attachment point 211 is different from the magnitude or phase of the modification of all the other attachment point in the apparatus, which include circuit components with different characteristics. In this manner, each attachment point provides a unique current/voltage signature allowing the controller 232 to monitor each attachment point, and to determine when a magnetic assembly device has been mounted into any of the attachment points.

Returning now to FIG. 2, the controller 232 may comprise ports, drivers, gate arrays, logic switches or other devices configurable to selectively energize one or more magnet assembly devices 212, 214, 216, 218 in response to an instruction set or command signal from a processor 234 of the control device 230 and to receive electrical signals therefrom and from attachment point 211, 213, 215, 217. In one implementation, the controller 232 and processor 234 are part of a single computing device. In other implementations, the controller 232 and processor 234 can be housed in separate devices that are electrically connected.

The control device 230 can be a desktop or workstation class computer that executes a commercially available operating system, e.g., MICROSOFT WINDOWS, APPLE OSX, UNIX or Linux based operating system implementations. In accordance with further embodiments, the control device 230 can be a portable computing device such as a smartphone, wearable or tablet class device. For example, the control 230 can be an APPLE IPAD/IPHONE mobile device, ANDROID mobile device or other commercially available mobile electronic device configured to carry out the processes described herein. In other embodiments, the control device 230 comprises custom or non-standard hardware configurations. For instance, the control device 230 can comprise one or more micro-computer(s) operating alone or in concert within a collection of such devices, network adaptors and interfaces(s) operating in a distributed, but cooperative, manner, or array of other micro-computing elements, computer-on-chip(s), prototyping devices, "hobby" computing elements, home entertainment consoles and/or other hardware.

The control device 230 can be equipped with a persistent memory device 236 that is operative to store the operating system in addition to one or more of software modules, such as those described herein to implement transcranial magnetic stimulation in accordance with embodiments of the present invention. In one embodiment of the present invention, the modules utilized by the control device 230 comprise software program code and data that are executed or otherwise used by the processor 234, thereby causing the control device 230 to perform various actions dictated by the software code of the various modules. The control device can also be in communication with a persistent data store that is located remotely and is accessible over a computer network via a network interface 238, which implements communication frameworks and protocols that are well known to those of skill in the art.

In certain embodiments, the persistent memory device 236 contains transcranial magnetic stimulation application program code 242 and blockchain interaction application code 244 (described further below). The control device also includes a library of treatment protocol units 240 for execution by the processor 234 in governing the operational parameters of the magnetic assembly devices. The treatment protocol units (TPUs) are, in one arrangement, data objects detailing specific operational characteristics that are implementable by the magnetic assembly devices. As is described in greater detail herein, one or more TPUs may be sequentially combined to form a treatment protocol. TPUs can be created locally or downloaded through the interface 238 from a remote site.

The operational parameters of a given TPU comprise a series of key-value pairs that users can define and which control operation of one or more magnetic assembly devices. More generally, a treatment protocol unit defines the manner in which one (and more typically at least two) or more magnetic assembly devices are activated to create electric fields across various areas of the brain of a subject over a window of time. Such information is used by the transcranial magnetic stimulation application program code to instruct the processor as to the manner in which to energize, via the controller, the set of magnetic assembly devices to create such a field. The one or more TPUs include instructions to the controller for generating signals that cause individual magnetic assembly devices to rotate. Receipt of such signals from the controller by a given magnetic assembly device causes its actuator to rotate its associated magnet at a particular frequency for a particular duration. Such rotation of the magnet at a set frequency results in the generation of a desired electric field within the brain, which may be used as part of a therapy, diagnosis, mapping or other medical diagnostic treatment.

Advantageously, the transcranial magnetic stimulation application program code allows the user to select sets of treatment protocol units (TPUs) from library 240 to form one or more treatment protocols. The TPUs can be considered as "units of stimulation" that can be combined to implement specific treatments, referred to collectively as treatment protocols. A user interface can be provided by the transcranial magnetic stimulation application program code, for example a graphical user interface (GUI) or a text-based interface. Through the user interface, the user can define a set of TPUs that the processor applies to the subject as a set treatment protocol, or can select a preset protocol comprising a set of TPUs defined locally or otherwise provided to the controller 230 from a remote site. As one example, in a neurological medical facility, a doctor or other medical professional can treat a patient with Parkinson's disease by selecting a treatment protocol from the TPU library 240 tailored for this condition.

According to one embodiment, the transcranial magnetic stimulation application program code serially applies the TPUs comprising a treatment protocol (e.g, like a script). Alternatively, the transcranial magnetic stimulation application program code may dynamically arrange and apply the treatment protocol units comprising a given treatment protocol. Still further, the processor may execute and apply certain treat protocol units in parallel, e.g., at the same time. The user may also share treatment protocols and TPUs with other users on other control devices by way of a network that the control device accesses via its network interface, which may further comprise receiving the individual treatment protocol units comprising a received treatment protocol.

In one particular arrangement, the transcranial magnetic stimulation application program code instructs the processor 234 of the control device 230 to apply a treatment that utilizes one or more particular magnetic assembly devices. The transcranial magnetic stimulation application program code can instruct the processor 234 to control the energization of all, or a portion of the magnetic assembly devices positioned on the transcranial system. An exemplary treatment protocol can involve a specific pattern of TPUs, the application of which is directed to the magnetic assembly device positioned in proximity to one or more areas of the subject's brain, such as the Broca's Area. The processor executing the transcranial magnetic stimulation application program code can generate a single control signal for distribution by the controller that details the desired rotation frequencies, durations, quiescent periods or other conditions for each of the magnetic assemblies. In other words, the user can select a treatment protocol and cause the system to implement a treatment, diagnosis, mapping, or other procedure, and so on by implementing the pattern of treatment protocol units, in parallel or serial, all based on the selection of a particular treatment protocol.

A TPU can be represented as a data object which serves to provide structure to a set of data regarding a treatment protocol, such as but not limited to, rotation frequency, motor energization duration, quiescent period and specific energizing of a particular set of zero or more magnetic assembly devices. The TPU is processed by the TMS application code 242 to establish the drive or quiescent settings for each magnetic assembly device. TPUs can include a frequency value representing a rotational frequency for one or more magnetic assembly devices, a rotational duration, a placement area for application of the treatment protocol unit and a quiescent period, as example properties. TPUs can also implement a Theta Burst Stimulation (TBS) protocol. Here, the TBS protocol is defined as one or more active TPUs followed by a second, quiescent TPU. In one particular example, the active TPU(s) defines a three (3) pulse pattern delivered at a frequency of 50 Hz, each pulse lasting 20 ms. A quiescent TPU lasting 160 ms defines an inter-burst interval from the last burst of the present pattern to the first burst of the next pattern. The active and quiescent TPSs combined for a repeating treatment pattern of having a duration of 200 milliseconds. While a single TPU can define a multiple burst pattern, it is also envisioned that the active TPUs defines a single burst. Thus, a collection of single burst TPUs (each without a period of quiescence following the burst) followed by a single or collection of quiescent TPUs can also be used to define a TBS protocol.

In one or more implementations, execution of a particular TPU in a treatment protocol can cause issuance of a command to a single magnetic assembly device for treating a localized area. Similarly, a given treatment protocol unit may identify a set of one or more magnetic assembly devices on the basis of the location(s) of such magnetic device assembly on the head mount which energize for rotation over a period of time on the basis of the instructions in the given treatment protocol unit that the processor at the control device interprets. In another arrangement, magnetic assembly devices can be addressable on the basis of its connection point to the head mount, with the location of the magnetic device assembly being defined as a result of its connection to the head mount by virtue of the attachment points. As a related matter, signal feedback concerning the operational capabilities/status of the magnetic assembly devices that are attached to the head mount and their attachment points can coordinate with the system so as to permit treatment protocols to be selected, and to inform the clinician or other treatment provider, patient or other user that additional or different magnetic assembly devices have to be attached, and where they have to be attached, before a particular treatment protocol is initiated.

As noted previously, a given TPU identifies one or more particular key-value pairs that ultimately instruct the operational state of a magnetic assembly device at a given point in time. Accordingly, a given TPU need not define each key-value pair contained within a given treatment protocol unit, e.g., some keys can have a null or empty value. For example, a TPU can provide information about a quiescent period free of any energization state information, e.g., frequency and duration values are set to null. In such a configuration, a quiescence-only TPU operates as a break or spacer in the active sessions of a treatment protocol. In this way, quiescent periods can be introduced to accompany treatment protocol units lacking a quiescent period. By way of example, treatment protocol units that only define a quiescent period can be used to ensure that there is a set repetition frequency of between 0.1 to 2 Hertz.

A treatment for a particular condition can be implemented as a group of TPUs. According to one embodiment, the transcranial magnetic stimulation application program code instructs the processor to configure or assemble a set of TPUs according to an overall desired length of treatment. For example, if the desired treatment is two minutes, the transcranial magnetic stimulation application program code instructs the processor to assemble the TPUs into a treatment protocol is of the desired length, such as by looping the TPUs that comprise the treatment protocol until the treatment duration has been achieved. Alternatively, longer duration TPUs can be used in a given treatment protocol to provide a treatment program of a desired length. The resulting treatment protocol is a data object containing data used to instruct all or a portion of the magnetic assembly devices to generate a specific series of electric fields within the brain of the subject. Where different magnetic assembly devices mounted to the same cap 205 have different treatment protocol units applied, a treatment program dataset is created, which may be saved in a persistent data store as a library of treatment protocols. Thus, a collection of treatment protocols can be generated whereby different individual treatment protocols are used to control one or more specific magnetic assembly devices at any given time.

As described throughout, the processor at the control device executes the transcranial magnetic stimulation program code to variably energize one (and more typically two) or more magnetic assembly devices spaced on the head mount 102 at locations that span at least a portion of the cranium of a subject. The control device provides functionality for user selection of one or more treatment protocols through interaction with the interface that the processor presents on a display device. The control device 230 may provide access to treatment protocols from local storage, as well as treatment protocols on remote data stores. According to one embodiment, the control device accesses a remote data store via a network through use of the network interface 238. Upon connection to the remote data store, the control device copies the transaction protocol to local storage for execution by the processor. Alternatively, the control device accesses the remote data store and reads transaction protocol information as needed, e.g., remote execution of the data.

The user can be presented with a listing of available treatment protocols, which may also comprise a listing of the individual treatment protocol units making up a given treatment protocol. Selection of a given treatment protocol can be made on the basis of applying a treatment directed towards a particular ailment. For example, a drop down menu can be provided in one embodiment by a graphical user interface that can list i) a set of exemplary potential ailments that require treatment, e.g.: depression, neurological and psychiatric disorders, migraines, aphasia, anxiety, Parkinson's disease, tinnitus, autism, schizophrenia, Alzheimer's, ALS, stroke (e.g. ischemic), Myotonic Dystrophy type 1 (DM1), stuttering, epilepsy, Parkinson's disease, pain and dystonia, cocaine, opioid and other addictive behaviors; ii) non-medical stimulation treatments such as for improved concentration, short and long-term memory, learning, foreign language training, etc. A user can select a treatment protocol (comprising one or more treatment protocol units) that has been previously designed by another user, and possibly already verified by peers, to ameliorate such conditions, or provide such stimulus treatments. Alternatively, the user is free to select one or more treatment protocol units depending on specific conditions or circumstances, for example, one or more collections of treatment protocol units may be presented as having applicability to a particular ailment, such as addiction or pain. The data store that maintains the treatment protocols and/or treatment protocol units can by associated with metadata that functions as a suggestion as to the applicability of a given treatment protocol unit or treatment protocol.

Optionally, information can be received from a database over the network interface which can define (e.g., constrain) the selection of treatment protocols to those that correspond to a prescription by a clinician or other treatment provider. Optionally, the set of treatment protocols available for selection can be defined (e.g., constrained) as a function of prior treatments. For instance, a treatment protocol can comprise a regimen of treatments in which the duration, energy, or other parameters are established for a patient or other user, yet which vary over the course of treatment. In this way, a predefined regimen of treatment can be implemented (and repeated with the same or other subjects) with precision by virtue of providing a series of treatment protocols through a predefined regimen.

During operation, the processor executes transcranial magnetic stimulation program code 242 and retrieves TPUs from library 240 for execution in series or in parallel. Upon execution of the TPUs, the processor issues instructions to the controller to activate (or deactivate as the case may be) specific magnetic assembly devices which causes the motor or other actuator within a given magnetic assembly device to energize and induce the desired electrical fields within the brain of the wearer or to de-energize, as the case may be.

Per the discussion of transcranial magnetic stimulation using treatment protocols above, it can be appreciated that the proper functioning of each of the actuated magnetic assembly devices is crucial in order to deliver treatments as intended. To ensure that the transcranial magnetic stimulation apparatus performs properly on a regular basis, the providers of the magnetic assembly devices can stipulate limitations on the use of the devices by licensed use restrictions. For example, a magnetic assembly device can be licensed for a particular treatment protocol, for example, for treating Parkinson's disease, and the device can be licensed for a threshold number of uses under the license. For example, an assembly licensed for a Parkinson's treatment protocol can be limited to 20 uses. While a centralized permission server can be used to ensure that the magnetic assembly devices are used only under the licensed restrictions, this solution requires connectivity with a permission server at every instance in which a magnetic assembly is used during a treatment. To avoid this dependence on connectivity with a central authorizing entity, one embodiment of the invention uses a blockchain methodology to manage, monitor and control the usage of the magnetic assembly devices to ensure only licensed devices are used, and that the licensed devices are used for only the permitted number of licensed treatments.

Identification of Magnetic Assembly Devices

As noted above, it is important to ensure that the magnetic assembly devices used in applying a treatment protocol are suitable for the purposes intended. To ensure that proper magnetic devices are employed, it is important for the TMS system to be able to verify: a) that for a given treatment protocol, the required number of magnetic assembly devices are positioned at correct attachment points on the head mount; b) that each magnetic assembly device is constructed to perform the specific treatment protocol; and c) that the end user (controller) is authorized to perform the TMS stimulation with the provided devices. Table I lists three medical conditions along with the number of magnetic assembly devices (MADs), the placement of the MADs with respect to the cranium on the head mount, and placeholders for stimulation parameters for treating each condition with a TMS. It is noted that the data presented in Table I is merely for illustrative purposes and is not meant to indicate the suitable locations for placement of magnetic device assemblies or any particular set of stimulation parameters or treatment protocol for the conditions listed. While the Table lists medical treatment protocols, as noted above, the TMS treatment protocols, in general, are not limited to medical uses. This information can be stored locally at the control device or can be stored or cached in one or more locations on an accessible network (e.g., a cloud platform).

| TREATMENT PROTOCOL | # of MADs | Locations of Devices | STIMULATION PARAMETERS | | | |
|---|---|---|---|---|---|---|
| | | | Frequency | Current | Voltage | Duration |
| Stuttering | 4 | A, B, C, E | F1 | I1 | V1 | T1 |
| Parkinson's Disease | 4 | A, C, D, F | F2 | I2 | V2 | T2 |
| OCD | 5 | B, C, D, E, F | F3 | I3 | V3 | T3 |

Figure 1:
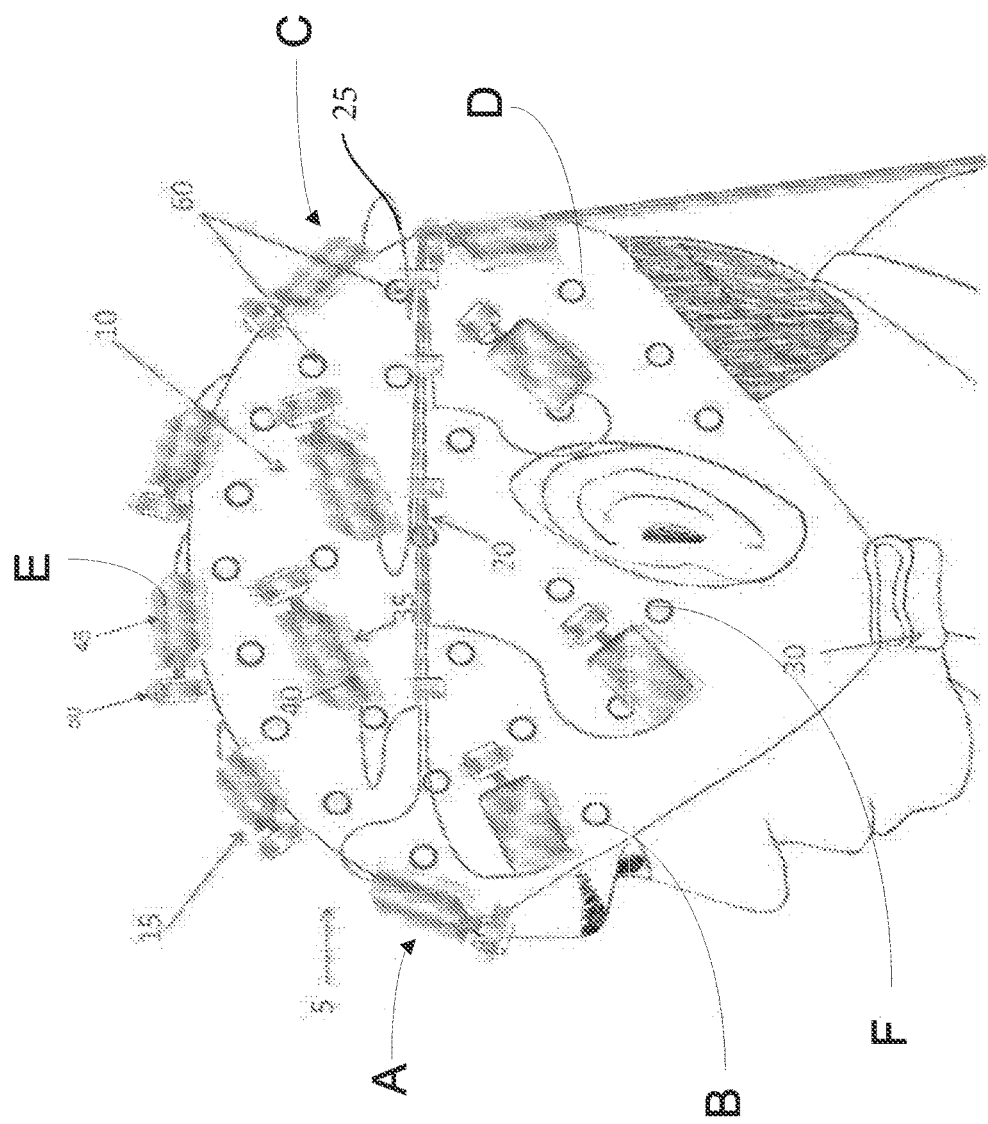
FIG. 1 is a side view of an example transcranial magnetic stimulation (TMS) apparatus that can be used in the context of the present invention.

The first row of Table I pertains to the medical (neurological) condition stuttering. For treating this condition, the treatment protocol employs four MADs, positioned at locations A, B, C and E (shown in FIG. 1); for this condition the controller activates the magnetic assembly devices using an electrical signal having requirements including a spin frequency F1, a current I1, a voltage V2 and a duration T1. The frequency can be a fundamental frequency for the entire stimulation signal or can characterize a portion of the stimulation signal, such as the maximum frequency for which the MADs must be rated. The current and voltage parameters can be maximum amplitudes, rms amplitudes or can be other current or voltage characteristics of the signal. Similarly, the duration can represent the entire duration of the stimulation signal, the duration of an oscillatory part of a signal, or a duration that includes multiple stimulation events.

The second row of Table I pertains to Parkinson's disease. The treatment protocol for this condition also calls for four magnetic assembly devices, but at locations, A, C, D, and F. Stimulation parameters are noted as values F2, I2, V2 and T2. The third row pertains to Obsessive Compulsive Disorder (OCD). The treatment protocol for this condition calls for the use of five magnetic assembly devices positioned at locations B, C, D, E and F. Another set of stimulation parameters F3, I3, V3 and T3 is noted.

Figure 4:
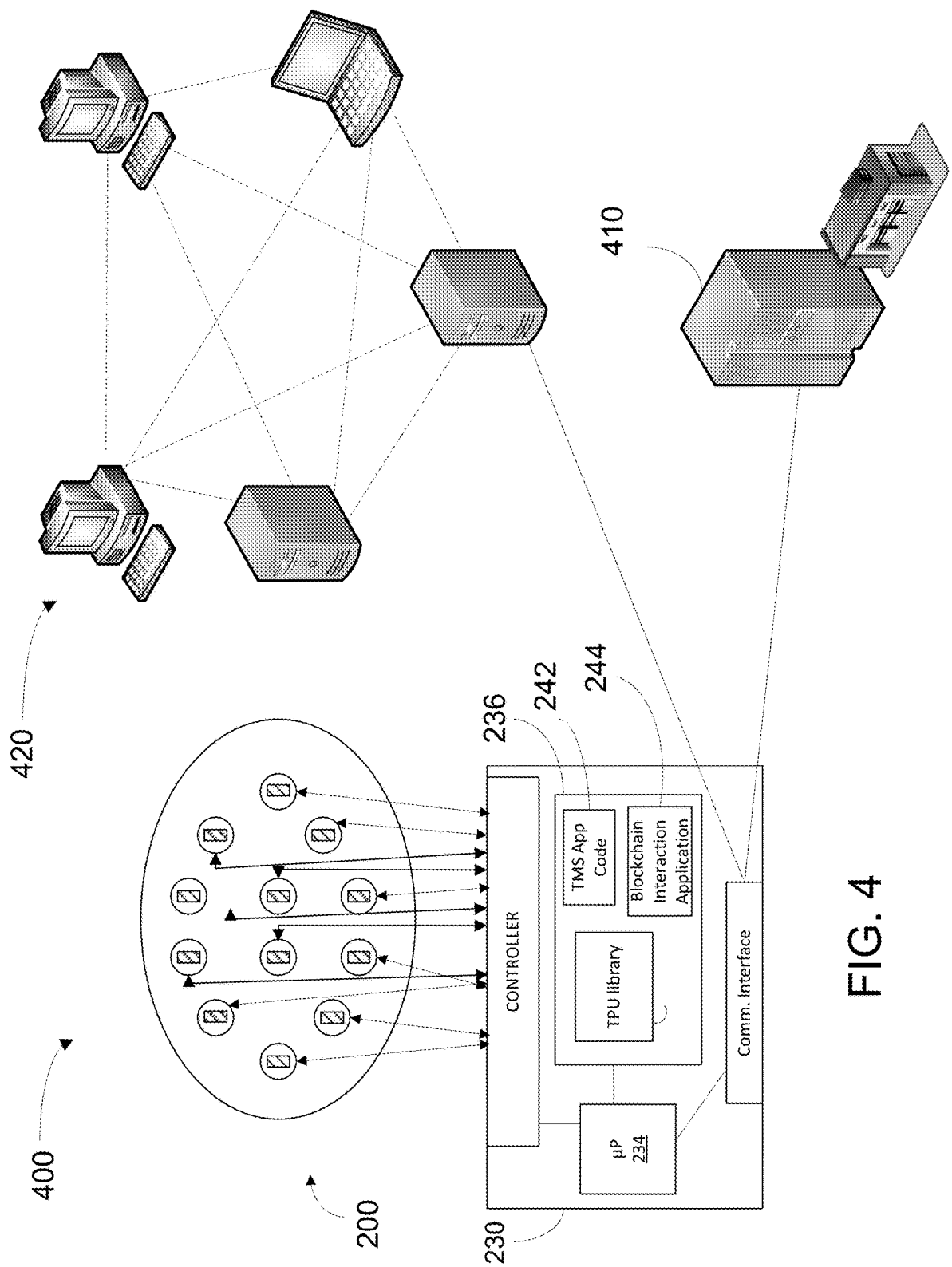
FIG. 4 is a schematic diagram that illustrates a system in which usage of licensed devices can be tracked using blockchain methods according to an embodiment of the present invention.

FIG. 4 is a schematic diagram that illustrates a system in which usage of licensed devices can be tracked using methods of the present invention. As shown in FIG. 4, the system 400 includes a transcranial magnetic system 200 having a TMS apparatus and control device as described above for "end user A", such as a medical treatment facility which houses a transcranial magnetic stimulation apparatus. End user A includes the TMS apparatus and the control device 230 which is communicatively coupled to a Vendor system 410 ("Vendor"), on an intermittent basis, and to a peer-to-peer network 420. In the depicted embodiment, the Vendor 410 is the entity that supplies magnetic assembly devices with particular constructions and unique identifiers to end user A. Vendor 410 assigns a unique product ID and one or more specific licensed use conditions for each magnetic assembly device that it provides. The unique product ID can be embedded in a bar code, QR code or RFID code that can be read optically. In addition, in some embodiments, the modified product ID can also be stored in a memory unit of the magnetic assembly device. As will be described further below, the stored modified product ID can be a pseudorandom code generated based on the product ID, in which the pseudorandom code generation used by the vendor 410 for this purpose is selected in view of the particular end user. In addition, in some embodiments, the Vendor can provide to the end user the identical algorithm for generating pseudorandom codes that is uses for that end user, which can be stored in persistent memory of the control device. For example, the product IDs can be used as seed data for the algorithm. The use of the pseudorandom code algorithm by the end user enables verification of the end user as being authorized to use the corresponding magnetic assembly devices for TMS treatments.

Table II below shows examples of licensed uses for four exemplary magnetic assembly devices that can be used in a transcranial magnetic system as described above. As indicated in the table, each magnet assembly device has a product ID, one or more licensed treatments for which the device can be used, and a corresponding number of permitted times the device can be employed for each licensed use. In the examples listed in Table II, a first magnetic assembly device is licensed for a Parkinson's disease treatment protocol and can be used in delivering 25 treatments (per the protocol). A second magnetic assembly device is licensed for two different treatments: obsessive compulsive disorder (OCD) and stuttering. The device can be used 15 times for delivering OCD treatments, or 15 times for delivering stuttering treatments, or 15 times for each of these treatments. A third magnetic assembly device, like the first device is also licensed for Parkinson's disease but has a more robust design and is therefore licensed for a greater number of uses (30). A fourth magnetic assembly device is licensed for treating Myotonic Dystrophy (type 1) and for 20 treatments.

TABLE II

| MAGNETIC ASSEMBLY PRODUCT ID | LICENSED USE | # OF PERMITTED USES |
|---|---|---|
| XM3A46F1 | Parkinson's disease | 25 |
| AJ287JI02 | Obsessive Compulsive Disorder | 15 |
| | Stuttering | 15 |
| CU192J7G | Parkinson's disease | 30 |
| GG98L61B | Myotonic Dystrophy type 1 (DM1) | 20 |

Returning again to FIG. 4, the Vendor 410 maintains a record indicating the identification, licensed uses and end user of each magnetic assembly it supplies. However, after the Vendor delivers the magnetic assembly devices to the end user of the transcranial magnetic assembly, the Vendor is not required to track uses of the devices, ensure compliance with licensed uses, or engage in other ongoing monitoring activities. The monitoring occurs onsite at the end user and can be verified by a blockchain methodology that removes the need for centralized control by the Vendor 410 or any other entity. Upon receipt of newly supplied magnetic assembly devices by the end user 200, the product ID, licensed use information, and number of permitted uses for each device is logged into and stored by the control device 230 at end user A.

Pseudorandom identification codes for each of the devices can be generated by executing an authorized pseudorandom code algorithm on the control device 230. The term "authorized" in this context means that the algorithm is provided by and/or controlled by the vendor 410, and that an authorized association between the end user and the vendor can be verified through the codes generated by the algorithm. The algorithm can be uploaded by the control device from the vendor, or otherwise provided to the end user, for example in a secure memory device from which the algorithm can be loaded by the control device.

The pseudorandom codes can be polynomial functions that expand a string x into a longer string f(x) that appears random. The codes can be made secure for encryption purposes by employing one-way functions, such as the RSA function, for f(x). The RSA function starts with a seed value ($x_0$); the following values can be calculated from the formula $x_i = x_i - 1^b$ mod n, in which n is a product of large prime numbers (p,q) set by the authorized algorithm. In certain implementations, the Product IDs of the magnetic assembly devices can be used as the seed value ($x_0$). The initial output values are the set $x_1, x_2 \ldots x_n$. The final output Y is a set of values $y_1, y_2 \ldots y_n$ that can be calculated as $y_i = x_i$ mode 2, which is a bit stream ($y_1 y_2 \ldots y_n$).

In setting up a TMS treatment at the end user, the head mount is placed on the subject and a selected treatment protocol is applied by placing a prescribed number of magnetic assembly devices on the attachment points determined by the protocol. Once the devices are installed, the TMS stimulation can be initiated by executing program code on the control device (e.g., via a user interface) to begin magnetic stimulation to the subject per the selected treatment protocol which is to be executed by the TMS application code 242. Prior to transmitting the electrical signals to induce the magnets to rotate, the control device determines, for instance one or more of the following: i) whether the number of magnets installed and their respective positions on the head mount match the requirements of the treatment protocol; ii) whether the magnets are licensed for the selected treatment protocol, and iii) whether the control device at end user A is authorized to perform the stimulation using the supplied magnetic devices.

When the magnetic assembly devices are installed at the end user, in one embodiment, the installation in the attachment points closes circuits, causing currents to be transmitted from the electrical leads of the attachment points to the control device. Because each attachment point has circuit components that mutually distinguish them from each other, the currents received by the control device act as signatures of the attachment locations in which the magnetic assembly devices have been installed. The TMS stimulation program includes code for causing the control device processor to compare the attachment points from which currents have been received to the attachment points prescribed by the treatment protocol which is stored in memory. If the sets of attachment points match, in terms of both the number of the devices and their positions on the head mount, the TMS stimulation program proceeds to the next determination. If the sets of attachment points do not match, the control device executing code of the TMS stimulation program issues a notification to the medical practitioner (e.g., a visual or audio notification via a user interface) that the magnetic assembly devices have not been installed in correct positions and stimulation of the devices is disabled. In other embodiments, the system can be configured to more simply request the user to manually conform via the interface that the MADs are installed in correct positions. In still another embodiment, no confirmation is made of MAD positions.

After verifying that the installed magnetic assembly devices are in proper position for the treatment to be delivered, if such verification is performed, the TMS stimulation program causes the control device to compare the licensed use information of the installed magnetic assembly devices with the treatment protocol. The installed magnetic assembly devices can be identified either manually or automatically. The TMS stimulation program code can include instructions for prompting user input or for polling the data from input ports of the control device. For example, the end user can scan the product ID of the devices that are installed in the head mount, and the scanned data can be transmitted or otherwise entered into the control device. In other implementations, conductive leads can be coupled to the magnetic assembly devices to read the product ID information from the memory units housed in the magnetic assembly devices. If the control device determines that the licensed use of the installed devices matches the treatment protocol, then the TMS stimulation program proceeds to the next determination step. Otherwise, the executed TMS stimulation program causes the control device to issue a notification that the magnetic devices installed are not licensed for the selected treatment, and the stimulation of the devices is disabled until this test is satisfied with a match.

Last, control device executes instructions of the TMS stimulation program that allows the control device to verify that the control device 230 is authorized to perform the treatment stimulation. The control device reads data in the memory units of the installed magnetic assembly devices to obtain the modified product ID information stored therein. The control unit then loads the pseudorandom codes generated by the algorithm received from the vendor. The TMS program instructions then cause the control unit to compare the modified product IDs with the pseudorandom codes. If there is a match between the modified product IDs and the pseudorandom codes, it can be concluded that the same algorithm, arising from the same source, generated both the modified product IDs stored on the devices and the pseudorandom code generated by the control device. This means that the end user and the vendor share the same algorithm, and the end user is therefore an authorized user of the magnetic assembly devices provided by the vendor. One advantage of this measure is that magnetic assembly devices cannot be used in a facility which does not have such authorization. If the end user is authorized, the TMS stimulation program enables stimulation according to the protocol, which then proceeds. If a match does not occur, stimulation is disabled.

It is noted that the steps performed by execution of the TMS simulation program described above can be performed in a different order.

Enforcement Using Blockchain Platform

In some embodiments, the control device at end user 200 is operative to execute a blockchain interaction application 244 (in FIG. 2) from code stored in memory. The blockchain interface application can be implemented using a number of different blockchain platforms such as Ethereum, Openchain and Hyperledger Fabric. These platforms enable the development of blockchain applications. Ethereum, for example, is a decentralized platform that supports "smart contracts" and is particularly useful for defining license restrictions.

Blockchain is a way of presenting transactions in an immutable distributed ledger that is effectively impossible to tamper with or retroactively change owing to the use of linked mathematical hash functions. A blockchain is an ordered sequence of "block." Each block includes a series of transactions that occur within a specified time period, along with other parameters such as hash values. The transactions are gathered into a block and added to the existing chain of blocks by participants in the peer-to-peer network 420, referred to as "miner." The distributed blockchain ledger is replicated and maintained in the peer-to-peer network 420. Importantly, the distributed ledger maintains a transparent history of all of the transactions in the blockchain which can thereafter be reviewed. The blockchain platform enables transactions to be posted to the distributed ledger, and also enables participants to validate posted transactions and to make calculations (sums, subtractions) based on the transactions stored in the ledger.

In the context of the present invention, a transaction can include: i) posting receipt from the vendor of a new magnetic assembly device with licensed treatments and usage numbers; ii) usage of a magnetic assembly device for a treatment and optionally iii), other changes to the license terms, such as permission to change a licensed treatment.

FIG. 5A shows a schematic illustration of an example blockchain transaction data block for posting the magnetic assembly devices listed in Table I. The data that is included in a particular block is configurable using functionality of the blockchain platform. In the case of FIG. 5A, the transactions posted are an initialization that reports the licensing terms of newly received magnetic assembly devices. The fields of the data block 500 include: a data block number (which in this case is 1); a poster entity, in this case end user A; transaction numbers that uniquely identify each and every transaction (listed as either new or used) and transaction data. In this example, the transaction data includes the relevant data for establishing the licensing terms to the blockchain. Each transaction includes a product ID number of a magnetic assembly device, the treatment(s) the device is licensed for, and number of uses of the device permitted for the licensed treatment(s). The posting type is "add" since the transactions reflect postings of newly received magnetic assembly devices and reflect additional treatment capability for end user A. Similarly, the transactions, labeled 1-4, are new and are not based on older, used transactions.

FIG. 5B and FIG. 5C show two examples of subsequent transaction data blocks. In FIG. 5B, a single transaction is shown. The transaction is new and numbered (5), following from the last transaction included in data block 1, which is numbered (4). Transaction (5) includes the product ID of the magnetic assembly (AJ2871102) a transaction type, "treatment (OCD)", and a number of uses, which in this case is two. This transaction can indicate, depending on the configuration of the blockchain interaction application, a request for use of the magnetic assembly identified as AJ2871102 in a treatment protocol for OCD two times during the relevant time period by end user A is being made, or alternatively, that magnetic assembly device AJ2871102 has already been used twice for treating OCD during the relevant period, and the use is being posted to the blockchain. In FIG. 5B, alongside "new" transaction (5) there is a "used" transaction (2) from data block 1. Transaction (2) is listed because the new transaction (5) requires and "uses" the initial licensed uses identified in the earlier transaction, data block 1. In addition, a special "bookkeeping" transaction (transaction 6) is listed in which the remaining uses allocated for treating OCD with device AJ287JI02, which is 13 (=15-2) is added back. In this manner the distributed ledger maintains a current record of the number of usages the magnetic assembly devices have left. In a similar manner, FIG. 5C includes a first transaction (transaction 7) having product ID GG98L61B, treatment (MYT), number of uses: 1, and a second transaction (transaction 9) having product ID XM3A46F1, treatment (PARK), and number of uses: 1. These transactions indicate that magnetic assembly identified as GG98L61B either is requested or was used in a treatment protocol for Myotonic Dystrophy once, and magnetic assembly identified as XM3A46F1 is being requested or was used in a treatment protocol for Parkinson's disease once during the relevant time period by end user A. Transaction 7 uses transaction 4 from data block 1, and transaction 9 uses transaction 1 from data block 1 in the manner described above. Both transactions have corresponding bookkeeping transactions in which the number of remaining usages (19 for device GG98L61B and 24 for device XM3A46F1) are recorded in the ledger.

Figure 6:
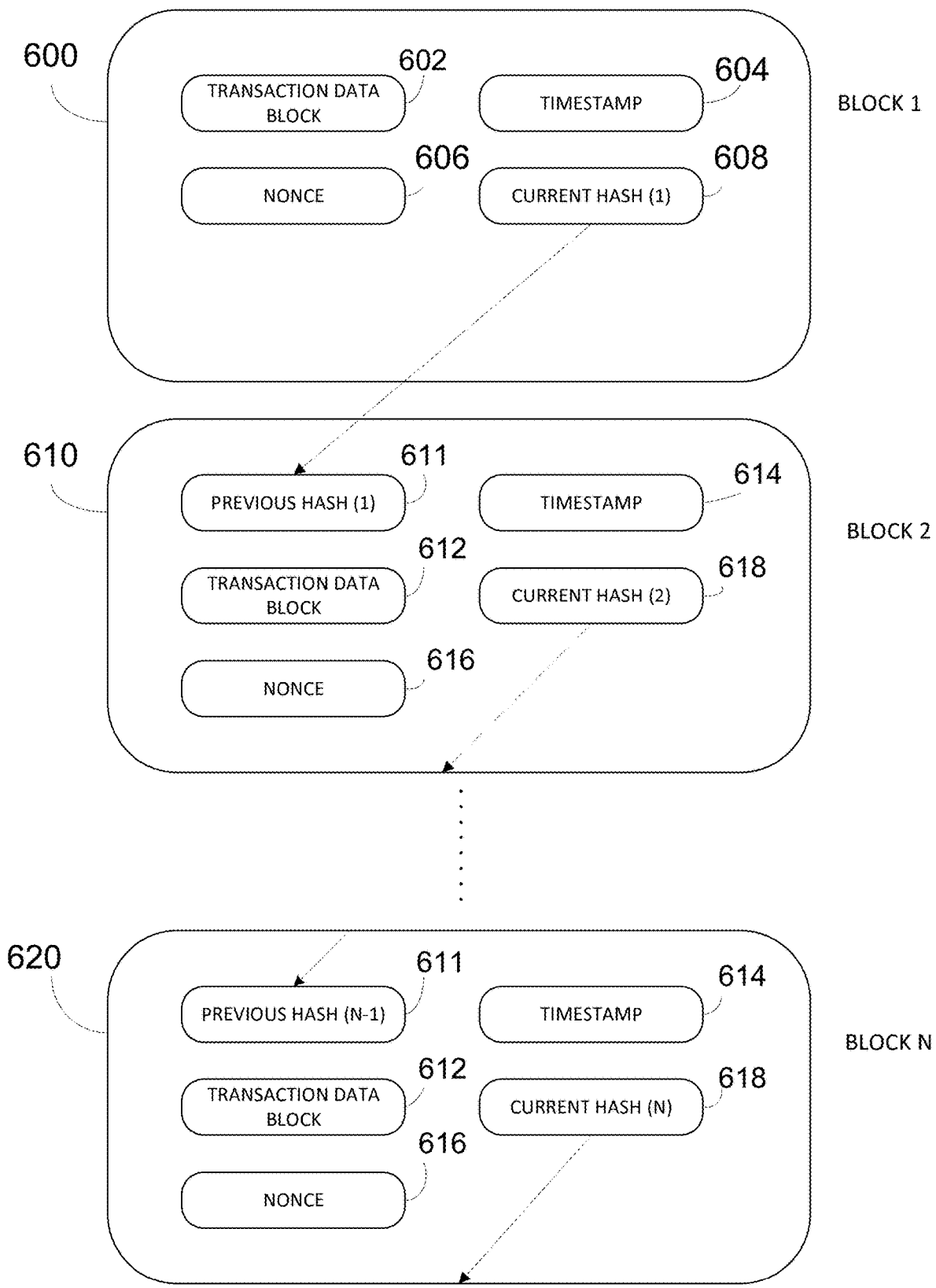
FIG. 6 is a schematic illustration of an example blockchain.

The transaction data, such as is illustrated in FIGS. 5A-5C, forms the substantive portion of the blocks that are included in a blockchain but there are several other important components that are included in each block. FIG. 6 is a schematic illustration of an example blockchain 600. A first block of the chain 600 has a block number of 1 and includes a transaction data block 602, a timestamp 604, a nonce value 606 (a random number), and a current hash value 608. The second block (Block 2) in the chain 610 has the next sequential block number (2). Block 610 includes as one field the current hash 611 of the previous Block (Block 1) which is included as a "previous hash (1)" indicating that it includes the hash of Block 1. In this manner the hash values of all of the blocks in the chain are linked. Block 2 similarly includes transaction data 612, timestamp 614, nonce value 616 and current hash 618. In the figure, an nth block 620 is shown, which is positioned some arbitrary number of links down the chain. Block 620 includes the previous hash 621 of block n−1 (not shown) as well as the other transaction data 622, timestamp 624, nonce 626 and current hash 628 fields. The current hash 628 of block N is shown pointing to the next block in the chain, which may not yet have been created if N is the latest block in the chain.

Blocks in the chain are created communally by miners in the peer-to-peer network 420 from transactions posted by the end users (e.g., 200) to the blockchain platform. When transactions are posted to the nodes of the network, each of the nodes collects the transactions that are posted within a specified into a block. In order for a node to have the block it creates accepted in the chain, the node has to solve what is known as the "proof of work" problem. A random number (the nonce) is proposed and appended to the data of the block and then the entire block, including the nonce, is hashed according to a known method such as SHA-256. If the resulting hash starts with a predetermined number of zeros, it is determined that a new block has been found. If not, the node substitutes a new nonce value for the previous value and recalculates the hash in an iterative process. Once the proof-of-work problem has been solved, the solving node broadcasts the block to the other nodes of the network. The block will be accepted, and appended to the blockchain, only once a majority of the nodes is able to validate the transactions in the block. Validation can be performed by any of the nodes because the ledger of transactions up to the point of the new block is freely available and transparent. Any of the nodes can check the chain to see if all transactions up until the current transactions are valid. For example, returning to the present context of TMS treatment, the nodes of the peer-to-peer network can readily determine from the ledger if a magnetic assembly device has no further uses left from the history of uses and could invalidate an additional use of the device. Moreover because of the linked hash values in the blocks, the chain cannot be altered. To alter a block in the chain, the proof-of-work problem would need to be solved not only for the altered block but also for all of the subsequent blocks in the chain, which is effectively impossible.

The blockchain interaction application 244 and blockchain platform can also implement logic used to monitor and enforce restrictions on the uses of the licensed devices using smart contracts. A smart contract herein can be defined as software logic that interacts with a blockchain or distributed ledger to determine, verify or enforce contractual obligations. Generally, licenses arranged between the vendor and the end user, such as the sale of magnetic assembly devices with licensed and limited use, can be implemented and monitored using blockchain technology. The use of blockchain technology enables management of the usage of licensed products through the combination of license transactions and smart contracts within the distributed network in a decentralized manner, precisely as described above, that is, to conform whether selected treatment protocol is appropriate for end user A using the identified magnetic assembly devices.

Figure 7:
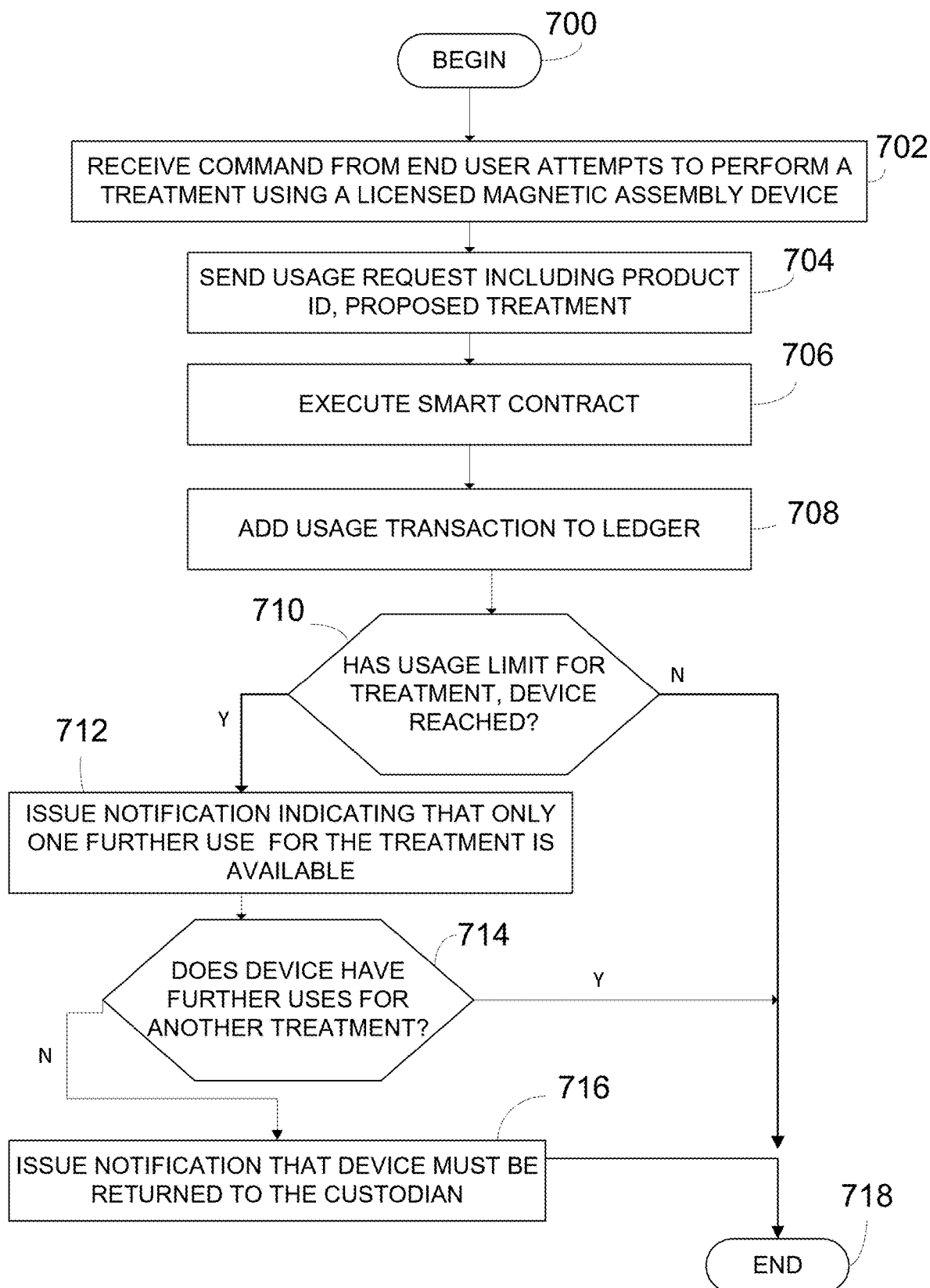
FIG. 7 is a flow chart of a method for managing a TMS apparatus including a plurality of magnetic assembly devices according to an embodiment of the present invention.

FIG. 7 is a flow chart of a method for managing a TMS apparatus including a plurality of magnetic assembly devices according to an embodiment of the present invention using a smart contract. The method begins in step 700. In step 702, the control device 230 receives a command from the end-user via the interface in an attempt to perform a treatment using one or more licensed magnetic assembly devices in a TMS system. In step 704, the blockchain interaction application 244 executed by the control device sends a usage request including the product ID and proposed treatment protocol. In step 706, the smart contract that corresponds to the usage transaction is executed by the blockchain platform. In step 708, the smart contract adds a usage transaction for a particular device and treatment to the distributed ledger. Following the addition of the transaction to the ledger, in step 710 the smart contract analyzes the ledger to determine if a usage limit corresponding to the product ID and treatment protocol has been reached. The limit is reached when further usage of the product would exceed the number of allowed usages governed by the currently in-force license. If the limit has been reached, then the associated smart contract may perform an enforcement action. Enforcement actions include sending notifications to the related parties including the custodian and the end user that the limit has been reached, for example. The smart contract policy can be set to allow one further use after the limit is reached. In the embodiment of the method shown in FIG. 7, if it is determined in step 710 that the limit is reached, the end user is alerted, in step 712, that they are permitted one further use of the device product for the requested licensed use. In step 714, the smart contract determines whether the product has further uses available for another treatment. If not, an additional, notification is issued in step 716 that the device has no further licensed uses available and that, after the final use, the device product must be returned to the custodian per the terms of the license. The notification can be sent to one or more of the end user, the custodian, and to members of the peer-to-peer network. The ledger can also be updated to reflect that a notification has been sent.

In addition to notification actions, the smart contract can further enforce the license terms by sending a command to the blockchain interaction application 244 to halt any further use of the magnet assembly device (either for the particular licensed use, or if no further uses are available at all, in general). For example, the smart contract can scan the ledger and determine that a "last use" notification has been sent previously, and that any further uses will be disallowed. The blockchain interaction application 244 is integrated into the control system at the end user site so as to be able to implement the smart control and prevent unlicensed uses of the magnetic assembly devices via the controller (in FIG. 2), for instance, by disabling the TMS application code 242 from operating. The method ends in step 718.

Optionally, the method of FIG. 7 can respond to a usage transaction at step 708 with notices or automated replenishment orders to end user A. This can better ensure that end user A has sufficient quantity of MADs which are rated for continued use. Preferably, each re-order by end user is followed by a return of exhausted MADs to the vendor 410 for examination, reconstruction, and testing so that MADs can be selectively recycled for uses in treatments having operating parameters that are within the long-term acceptable field conditions for a refurbished MAD.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to known registered marks representing various systems are cited throughout this application, the disclosures of which are incorporated herein by reference. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the claims that follow, the respective features recited in those points, and by equivalents of such features.

What is claimed is:

1. A head mount configured to support a plurality of removably mountable magnetic assembly devices for electrical connection to a controller, comprising:
   an interior sized to be seated on human head;
   an exterior with a plurality of attachment points; and
   a plurality of circuit components, each one of the plurality of circuit components being coupled to a corresponding one of the plurality of attachment points, each one of the plurality of circuit components providing a unique circuit response based on a magnetic assembly device being coupled to the corresponding attachment point of the circuit component;
   wherein upon coupling of a magnetic assembly device into any of the plurality attachment points, the response of the corresponding circuit component uniquely identifies the location of the attachment point at which the magnetic assembly device has been deployed;
   wherein the controller, upon receiving the response of the corresponding circuit component that uniquely identifies the location of the attachment point at which the magnetic assembly device has been deployed, is configured to determine whether to activate the magnetic assembly device coupled to the attachment point of the identified location in connection with a particular session in accordance with a transcranial magnetic stimulation treatment protocol for a given transcranial magnetic stimulation treatment.

2. The head mount of claim 1, wherein the circuit response is dictated solely by the circuit component.

3. The head mount of claim 1, wherein the circuit response is a function of both i) a second circuit component that is affixed to a magnetic assembly device joined to one of the plurality of attachment points and ii) the specific circuit component of the plurality that is coupled to the one of the plurality of attachment points.

4. The head mount of claim 1, wherein the circuit response is one of unique resistance, impedance, capacitance, and inductance.

5. The head mount of claim 1, further comprising electrical leads coupled to the attachment points.

* * * * *